United States Patent [19]
Kwong

[11] Patent Number: 5,254,541
[45] Date of Patent: Oct. 19, 1993

[54] (QUINOLIN-2-YLMETHOXY)INDOLE/CYCLODEXTRIN COMPLEX

[75] Inventor: Elizabeth Kwong, Pointe Claire, Canada

[73] Assignee: Merck Frosst Canada, Inc., Quebec, Canada

[21] Appl. No.: 793,059

[22] Filed: Nov. 15, 1991

[51] Int. Cl.$^5$ .................. A61K 31/715; A61K 31/47
[52] U.S. Cl. ..................................... 514/58; 514/314; 514/826
[58] Field of Search ................ 514/58, 314, 826; 536/103

[56] References Cited

U.S. PATENT DOCUMENTS

| | | | |
|---|---|---|---|
| 3,453,259 | 7/1969 | Paramerter et al. | 536/103 |
| 3,459,731 | 8/1969 | Gramera et al. | 536/103 |
| 4,727,064 | 2/1988 | Pitha | 514/58 |

FOREIGN PATENT DOCUMENTS

| | | |
|---|---|---|
| 0419049 | 3/1991 | European Pat. Off. |
| 0449167 | 10/1991 | European Pat. Off. |
| 0449731 | 10/1991 | European Pat. Off. |
| 3815902 | 11/1989 | Fed. Rep. of Germany |
| WO89/10739 | 11/1989 | PCT Int'l Appl. |

OTHER PUBLICATIONS

Szejtli, J., Starch, 33, No. 11, 387–390, 1981.
Atwood et al., Inclusion Compounds–Volume 3, Academic Press Inc., Ch. 11, 1984.
Loftsson et al. Inter. J. of Pharm., 67, R5–R7, 1991.
Loftsson, et al., Intl. J. Pharm. 57, 63–72 (1989).
Muller and Albers, J. Pharm. Sci. 80(6), 599–604 (1991).
Rao et al., J. Org. Chem., 56, 1327–1329 (1991).
Pitha et al., Int'l. J. Pharm. 29, 79–38 (1986).
Pitha et al., J. Pharm. Sci. 75(2), 165–167 (1986).
Chem. Abst. 115(19): 207870x, Prasit, EP419049 Mar. 27, 1991 to Merck Frosst Canada.
Martin *Physical Pharmacy* p. 324, 1983.

*Primary Examiner*—Frederick E. Waddell
*Assistant Examiner*—Gregory Hook
*Attorney, Agent, or Firm*—Joseph F. DiPrima

[57] ABSTRACT

A complex of cyclodextrin and 3-[N-(p-chlorobenzyl)-3-(t-buthylthio)-5-(quinolin-2-ylmethoxy)indol-2-yl]-2,2-dimethylpropanoic acid, sodium salt is more soluble in water than the sodium salt alone. The complex is useful as an anti-asthmatic, anti-allergic, anti-inflammatory, or cytoprotective agent. It is also useful in treating diarrhea, hypertension, angina, platelet aggregation, cerebral spasm, premature labor, spontaneous abortion, dysmenorrhea, and migraine.

3 Claims, No Drawings

(QUINOLIN-2-YLMETHOXY)INDOLE/CYCLODEXTRIN COMPLEX

BACKGROUND OF THE INVENTION

EP 419,049, Prasit et al., Mar. 27, 1991, describes a series of quinolin-2-ylmethoxy indoles useful as inhibitors of leukotriene biosynthesis. Examples 1 and 1A therein teach the synthesis of 3-[N-(p-chlorobenzyl)-3-(t-butylthio)-5-(quinolin-2-ylmethoxy)indol-2-yl]-2,2-dimethylpropanoic acid (L-686,708) as a crystalline compound. The sodium salt thereof, which is prepared by hydrolysing the methyl ester thereof with a base such as NaOH, can also be isolated as a crystalline solid which exhibits good solid state characteristics, such as non-hygroscopicity, physical stability, etc.; however, it exhibits very low aqueous solubility (approx. 0.005–0.03 mg/mL) and gives rise to low oral bioavailability.

SUMMARY OF THE INVENTION

A complex of cyclodextrin and the sodium salt of L-686,708, in the molar ratio 1–5:1 (optimally, 2.5:1), has now been found which exhibits a 26-fold increase in bioavailability over a simple mixture of cyclodextrin and the sodium salt.

DETAILED DESCRIPTION

By "cyclodextrin", as used herein, is meant 2-hydroxypropyl-$\beta$-cyclodextrin, which is a commercially available condensation product of $\beta$-cyclodextrin with propylene oxide, the preparation of which has been described (e.g., U.S. Pat. Nos. 3,459,731 and 3,453,259). $\beta$-cyclodextrin has the empirical formula $(C_6H_{10}O_5)_7$; and propylene oxide is $C_3H_6O$. The cyclodextrin used herein can thus be represented as $(C_6H_{10}O_5)_7 \cdot (C_3H_6O)_n$, wherein n is referred to as the Degree of Substitution (DOS). The average DOS of the cyclodextrin can be from 5 to 8, with an optimal value of 7. (See Pitha, et al., Int. J. Pharm., 1986, 29, pp. 73–82 for a further description of cyclodextrin).

The sodium salt of L-686,708 is a compound of the formula:

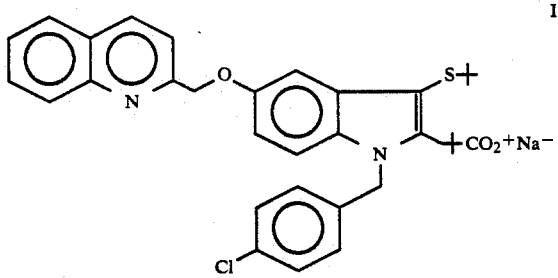

II

The complex is prepared by stirring the sodium salt of L-686,708 and cyclodextrin in the desired molar ratio in equal volumes of 0.01M ammonium hydroxide (pH=9) and one or more of a water-miscible organic solvent for 1 hour. Suitable organic solvents are methanol, ethanol, 2-propanol, acetone, acetonitrile, and the like, of which ethanol is preferred. The solution is then evaporated by vacuum and the residue redissolved in water and freeze dried. Alternatively, the redissolved residue can be spray dried.

The resultant complex retains the biological properties of the crystalline salt but is highly soluble in water. The complex is useful as an inhibitor of leukotriene biosynthesis in the same manner as described in EP 419,049 for L-686,708. Advantageously, it is much more bioavailable. EP 419,049 is incorporated herein by reference, especially pages 5–10, 25 and 26 thereof.

Therefore, one aspect of this invention is a pharmaceutical composition comprising a therapeutically effective amount of an L-686,708 sodium salt/cyclodextrin complex and a pharmaceutically acceptable carrier.

Another aspect is a pharmaceutical composition as described above additionally comprising an effective amount of a second active ingredient selected from the group consisting of non-steroidal anti-inflammatory drugs; peripheral analgesic agents; cyclooxygenase inhibitors; leukotriene antagonists; leukotriene biosynthesis inhibitors; $H_1$- or $H_2$-receptor antagonists; antihistaminic agents; prostaglandin antagonists; and ACE antagonists. Especially preferred is such a pharmaceutical composition wherein the second active ingredient is a non-steroidal anti-inflammatory drug. Also especially preferred is such a pharmaceutical composition wherein the weight ratio of L-686,708 sodium salt to said second active ingredient ranges from about 1000:1 to 1:1000.

Another aspect of this invention is a method of preventing the synthesis, the action, or the release of SRS-A or leukotrienes in a mammal which comprises administering to said mammal an effective amount of said complex, especially wherein the mammal is man.

Another aspect is a method of treating asthma in a mammal comprising administering to a mammal in need of such treatment a therapeutically effective amount of said complex, especially wherein the mammal is man.

Another aspect of this invention is a method of treating inflammatory diseases of the eye in a mammal which comprises administering to a mammal in need of such treatment a therapeutically effective amount of said complex, especially wherein the mammal is man.

The pharmaceutical compositions of the present invention comprise a complex, as described herein, as an active ingredient and may also contain a pharmaceutically acceptable carrier and optionally other therapeutic ingredients.

The compositions include compositions suitable for oral administration. They may be conveniently presented in unit dosage form and prepared by any of the methods well-known in the art of pharmacy.

In practical use, the complex can be combined as the active ingredient in intimate admixture with a pharmaceutical carrier according to conventional pharmaceutical compounding techniques. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administeration, tablets and capsules represent the most advantageous oral dosage unit form in which case solid pharmaceutical carriers are obviously employed. If desired, tablets may be coated by standard aqueous or nonaqueous techniques.

In addition, to the common dosage forms set out above, the complex may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more acessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the complex of this invention:

| Tablet | mg/tablet |
| --- | --- |
| Complex | 87.5 |
| Microcrystalline Cellulose | 352.5 |
| Povidone | 14.0 |
| Pregelatinized Starch | 43.5 |
| Magnesium Stearate | 2.5 |
|  | 500.0 |
| Capsule | mg/capsule |
| Complex | 87.5 |
| Lactose Powder | 511.0 |
| Magnesium Stearate | 1.5 |
|  | 600.0 |
| Capsule | mg/capsule |
| L-686,708, sodium salt/ cyclodextrin complex (1:2.5) | 350 |
| Microcrystalline cellulose | 90 |
| Pregelatinized Starch | 60 |
| Magnesium stearate | 5 |
| TOTAL | 505 |

The invention is further defined by reference to the following examples, which are intended to be illustrative and not limiting. Temperatures are in degrees Celsius.

Preparations 1 and 2 appear in EP 419,049 as Examples 1 and 1A and are copied here for convenience. Starting materials also appear in EP 419,049.

PREPARATION 1

3-[N-(p-Chlorobenzyl)-3-(t-butylthio)-5-(quinolin-2-ylmethoxy)indol-2-yl]-2,2-dimethylpropanoic acid

Step A:

3-[N-p-Chlorobenzyl-3-(t-butylthio)-5-methoxyindol-2-yl]-2,2-dimethylpropanoic acid methyl ester To a solution of 39 g of methyl 5-(t-butylthio)-2,2-dimethyl-4-oxopentanoate in a mixture of 300 mL of toluene and 150 mL of glacial acetic acid was added 15 g of NaOAc and 50 g of 1-(4-methoxyphenyl)-1-(p-chlorobenzyl)hydrazine hydrochloride. The reaction was maintained with stirring at room temperature for 3 days under argon in the dark. The mixture was poured into 3 L of $H_2O$ and extracted with $3 \times 500$ mL of EtOAc. The ethyl acetate was washed with $3 \times 500$ mL of water then solid $NaHCO_3$ was added. The mixture was filtered and the filtrate washed twice with water. The organic phase was dried over $MgSO_4$ and evaporated to dryness to provide the title compound. m.p. 102°–103° C.

Step B:

3-[N-(p-Chlorobenzyl)-3-(t-butylthio)-5-methoxyindol-2-yl]-2,2-dimethylpropanoic acid The compound from Step A was hydrolysed using 325 mL of THF, 600 mL of MeOH and 325 mL of 1.0M LiOH. The solution was heated to 80° C. for 3 h. The solution was acidified with 1N HCl and extracted with $3 \times 200$ mL of EtOAc. The organic phase was washed with water ($2 \times 150$ mL) and dried over $MgSO_4$. The solution was evaporated to dryness to provide the title compound. m.p. 190°–191° C.

Anal C, H, N: Calc. C 65.27; H 6.57; N 3.04; Found C 65.28; H 6.58; N 3.04.

Step C: Methyl 3-[N-(p-chlorobenzyl)-5-hydroxy-3-(t-butylthio)indol-2-yl]-2,2-dimethylpropanoate A solution of 61 mL of t-butylthiol in 650 mL of dry HMPA at 0° C. was treated portionwise with 26 g of 50% NaH in mineral oil after removal of oil with hexane. The reaction was stirred at RT for 30 mins and 46 g of the compound from Step B was added.

The reaction was then heated under $N_2$ at 175° C. for 5 hours. The solution was cooled, and poured onto crushed ice, after which it was treated with 2N HCl to pH 5 and extracted with EtOAc ($3 \times 500$ mL). The organic phase was washed with $H_2O$ ($3 \times 200$ mL) dried ($MgSO_4$) and evaporated. The residue was dissolved in 300 mL of ether and ethereal diazomethane was added until all acid was consumed. The excess solvent was removed and the oily residue triturated with hexane to leave a crystalline mass which was recrystallized from EtOAc/hexane to provide the title compound as a white crystalline solid, m.p. 170°–171° C.

Step D: Methyl 3-[N-(p-chlorobenzyl)-3-(t-butylthio)-5-(quinolin-2-ylmethoxy)indol-2-yl]-2,2-dimethylpropanoate.

Methyl 3-[N-(p-chlorobenzyl)-5-hydroxy-3-(t-butylthio)indol-2-yl]-2,2-dimethylpropanoate (33.6 g) from Step C was dissolved in 500 mL of dry DMF and the solution was charged with 2.4 g of KI, 30.3 g of $K_2CO_3$, 4.77 g of $Cs_2CO_3$ and 23.5 g of 2-(chloromethyl) quinoline hydrochloride. The reaction was stirred at RT, under $N_2$, for 72 hours then it was poured into water (1.5 L), acidified with 1N HCl and extracted (3×200 mL) with $CH_2Cl_2$. The organic phase was washed with $H_2O$ (3×150 mL), dried and evaporated. The residue was dissolved in hot EtOAc and upon cooling crystallized to deposit 22.0 g of the title compound, m.p. 166°–167° C.

Step E:
3-[N-(p-Chlorobenzyl)-3-(t-butylthio)-5-(quinolin-2-ylmethoxy)indol-2-yl]-2,2-dimethylpropanoic acid Using the hydrolytic procedure of Step B but substituting the ether of Step D for the ester of Step A provided the title compound, which was recrystallized from 1:1 EtOAc/hexane. m.p. 208° C.

Anal C, H, N: Calc. C 69.55; H 6.01; N 4.77; Found C 69.77; H 6.05; N 4.70.

PREPARATION 2

3-[N-(p-Chlorobenzyl)-3-(t-butylthio)-5-(quinolin-2-ylmethoxy)indol-2-yl]-2,2-dimethylpropanoic acid Step A: N-Acetyl-4-(quinolin-2-ylmethoxy)aniline A mixture containing 2-(chloromethyl)quinoline hydrochloride (100.0 g), 4-acetamidophenol (70.69 g) and milled anhydrous potassium carbonate (194 g) was stirred in DMF (1.2 L) using a mechanical stirrer for 48 hours. The mixture was carefully poured onto ice/water (3 L) with vigourous stirring. After the ice had melted, the solid was filtered and rinsed thoroughly with water. It was recrystallized from 95% ethanol and filtered to give the title compound in three crops.

Step B: 4-(Quinolin-2-ylmethoxy)aniline

A suspension of N-acetyl-4-(quinolin-2-ylmethoxy)aniline (Step A, 108.9 g) in 1 L of 95% ethanol containing 10M KOH (120 mL) was heated at reflux under nitrogen in a heating mantle. When the hydrolysis was complete (approx. 36 h), the reaction mixture was cooled and ethanol was partially removed under vacuum. The mixture was then diluted with water (200 mL) and the fine off-white crystals were collected and thoroughly rinsed with water. The material, after air-drying, yielding the title compound which was used as such in the next step.

Step C: 4-(Quinolin-2-ylmethoxy)phenylhydrazine

A quantity of 84 g of 4-(quinolin-2-ylmethoxy)aniline from Step B was suspended in 300 mL of deionized $H_2O$ and 84 mL of 12M HCl. The suspension was stirred vigourously to obtain a fine particle suspension. Then a precooled solution (5° C.) of 23.88 g of sodium nitrite dissolved in 75 mL of deionized $H_2O$ was added dropwise to the suspension at 5° C. over 25 minutes. The solution was stirred at 5° C. for 60 min to obtain the diazonium salt as a clear brown solution. The presence of excess $HNO_2$ was confirmed by KI-starch paper, and the pH of the solution was about 3.0. If a white suspension persisted after 1 h, the mixture was filtered through a glass wool plug, to give the diazonium salt in the filtrate.

In the meantime a sodium hydrosulfite solution was prepared by dissolving 321 g of sodium hydrosulfite (approx. 85% purity) in 2 L of deionized water, and cooled at 0° to 5° C. To this solution were added 15 mL of 2N NaOH and 2 L of ether. The biphasic solution was kept near 0° C. by addition of crushed ice and was stirred vigourously. To this solution was added dropwise the diazonium salt solution with stirring maintained throughout. At the end of the addition an orange solid was formed and 600 mL of NaOH (2N) was added over 30 minutes. The reaction was finally stirred for 60 minutes at 25° C. The solid was collected, suspended in ether (1 L) and filtered. The process was repeated with 2 L of water to yield the title compound as a pale yellow solid after freeze-drying overnight. m.p. 73°–85° C. (dec).

Step D:
1-(p-Chlorobenzyl)-1-[4-(quinolin-2-yl-methoxy)-phenyl]hydrazine

A quantity of 10 g of 4-(quinolin-2-ylmethoxy)-phenylhydrazine from Step C was added to a solution of 10.5 mL of diisopropylethylamine and 150 mL of $CH_2Cl_2$. To the yellow suspension was added 9.11 g of p-chlorobenzyl chloride followed by 3.64 g of $Bu_4NBr$ and 50 mL of $CH_2Cl_2$. The reaction was stirred for approximately 24 hours. When no starting material remained, the reaction was diluted with $H_2O$ and extracted 3 times with $CH_2Cl_2$. The combined organic phase was washed once with water and dried ($MgSO_4$), filtered and evaporated to dryness. The solid residue was dried under vacuum overnight prior to being swished in ether/methanol 90/10 to give the title compound as a pale yellow solid. m.p. 130° C.

Step E:
3-[N-(p-Chlorobenzyl)-3-(t-butylthio)-5-(quinolin-2-ylmethoxy)indol-2-yl]-2,2-dimethylpropanoic acid The methyl ester of the title compound was prepared according to the method described in Step A of Example 1 but using the phenylhydrazine from Step D of Example 1A as starting material.

The title compound was prepared under the conditions described in Step B of Example 1.

PREPARATION 3

Crystalline
3-[N-(p-chlorobenzyl)-3-(t-butylthio)-5-(quinolin-2-ylmethoxy)indol-2-yl]-2.2-dimethylpropanoic acid, sodium salt (L-708 Na+ Salt by Hydrolysis of Ester)

A mixture of the methyl ester of the title acid (Preparation 1, Step D) (6.25 kg, 10.4 moles) and EtOH (absolute, 45 L) was warmed to 50° C. and a solution of NaOH (2.29 L of a 5N solution, 11.4 moles) in $H_2O$ (5 L) was added. The reaction was heated to reflux and held at this temperature for 41 hours. The progress of the reaction was monitored by HPLC using a Zorbax RX column, a mobile phase consisting of 0.1% phosphoric acid:acetonitrile (20:80) at 1.15 mL/min, with UV detection at 220 nm. Additional NaOH (103.8 mL of a 5N solution, 0.52 moles) was added and the reaction was held at reflux for 24 hours, then cooled to 60° C. EtOH:H20 (25 L of a 90:10 mixture) was added and the reaction was filtered. The filtrate was azeotropically distilled to remove the water. Ethanol was added, as needed, during the distillation to maintain the volume above 62.5 L. The distillation was monitored for water content by Karl Fischer titration. The reaction was concentrated to 37.5 L, cooled to room temperature, then filtered. The filter cake was washed with cold (5° C.) EtOH (5×3.75 L) and dried under vacuum at 50° C. for 72 hours, providing 5.58 kg of the title compound (88% yield).

EXAMPLE 1

Cyclodextrin Complex

The sodium salt of L-686,708 (Preparation 3) (1.5 g) was added to 75 mL absolute ethanol and stirred until it dissolved. Then 2-hydroxypropyl-$\beta$-cyclodextrin (Pharmatec) (3.75 g) was added and the solution basified using 75 mL ammonium hydroxide (0.01M, pH=9). The flask was stoppered and stirred for another hour at room temperature. The clear homogenous solution was evaporated in vacuo using a rotary evaporator (Brinkmann model Rotavapor R). The residue was redissolved in 25 mL water and freeze dried in a lyophilizer (VirTis model 10SRC) to yield the complex as a white, amorphous powder.

That the product was in the form of a complex was evidenced by the measurement of intrinsic solubility and differential scanning calorimetry.

Phase solubility experiments were conducted by adding excess amounts (20 mg/mL) of L-686,708, sodium salt, to aqueous solutions (pH=9) containing various amounts of cyclodextrin and mixing on a rotating mixer. After equilibration at room temperature for at least 48 hrs, aliquots of the mixture were centrifuged to separate the undissolved sodium salt. The supernatant was diluted and dissolved L-686,708 concentration measured by HPLC. The solubility curve, which shows the effect of cyclodextrin on the aqueous solubility of L-686,708 sodium salt, is of Higuchi's $A_n$-type (Higuchi and Connors, Advances in Analytical Chemistry and Instrumentation, Reilly, C.N. (ed.), Inter Science, New York, 1965, pp 117-212), which shows that at higher cyclodextrin concentration solubility of L-686,708, sodium salt, did not increase as much as at lower cyclodextrin concentration. The stability constant of the complex as calculated from the initial straight line portion of the phase solubility diagrams was high (3.51 $mM^{-1}$). This stability constant is a tentative measure of complex formation.

Thermographs obtained via DSC for L-686,708 sodium salt, and the complex thereof showed the disappearance of an L-686,708, sodium salt, peak when the complex was formed.

An oral administration of the complex to rats gave a higher maximum achievable plasma concentration ($C_{max}$) of drug than that achieved with a similar dose of the compound physically mixed with cyclodextrin. The AUC of the complex was found to be 26 fold higher than that of the mixture, as shown in Table 1-1.

TABLE 1-1

| Pharmacokinetic Parameter | Complex | Physical Mix |
|---|---|---|
| $C_{max}$ (µg/mL) | 4.9 ± 2.6 | 0.4 ± 0.3 |
| AUC* (µg x/h/mL) | 44.6 ± 14.5 | 1.69 ± 0.44 |

*Area under plasma concentration-time curve.

Bioavailability Protocol

The freeze dried complex was dissolved in water to a concentration of 20 mg/mL of L-686,708, sodium salt.

Four male Sprague Dawley rats weighing approximately 400 g were fasted overnight and given an oral dose by gavage of the above dosing solution (100 mg/kg). Blood samples were withdrawn from the jugular vein at designated time intervals of 0, 0.25, 0.5, 1, 2, 4, 6, 8, and 24 hours. Plasma samples were frozen until analysis.

EXAMPLE 2

Solid Dosage Formulation

| | Amounts (mg) |
|---|---|
| L-686,708, sodium salt/ cyclodextrin complex (1:2.5) | 350 |
| Microcrystalline cellulose | 90 |
| Pregelatinized Starch | 60 |
| Magnesium stearate | 5 |
| TOTAL | 505 |

The ingredients from the table are mixed and filled into hard gelatin capsules.

What is claimed is

1. A complex of 2-hydroxpropyl-B-cyclodextrin and 3-[N-(p-chlorobenzyl)-3-(t-butylthio)-5(quinolin-2-ylmethoxy)indol-2-yl]-2,2-dimethylpropanoic acid, sodium salt in the molar ratio 1-5:1.

2. A complex of claim 1 wherein the molar ratio is 2.5:1.

3. A pharmaceutical composition comprising a therapeutically effective amount of a complex of claim 1 and a pharmaceutically acceptable carrier.

* * * * *